(12) United States Patent
Tomizawa et al.

(10) Patent No.: US 12,033,356 B2
(45) Date of Patent: Jul. 9, 2024

(54) COEFFICIENT DETERMINATION DEVICE, PIGMENT CONCENTRATION CALCULATION DEVICE, COEFFICIENT DETERMINATION METHOD, AND NON-TRANSITORY COMPUTER-READABLE STORAGE MEDIUM

(71) Applicant: SHARP KABUSHIKI KAISHA, Sakai (JP)

(72) Inventors: Ryota Tomizawa, Sakai (JP); Yoshihisa Adachi, Sakai (JP); Yuki Edo, Sakai (JP); Rieko Ogawa, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 557 days.

(21) Appl. No.: 17/287,247

(22) PCT Filed: Oct. 4, 2019

(86) PCT No.: PCT/JP2019/039318
§ 371 (c)(1),
(2) Date: Apr. 21, 2021

(87) PCT Pub. No.: WO2020/090348
PCT Pub. Date: May 7, 2020

(65) Prior Publication Data
US 2021/0383571 A1 Dec. 9, 2021

(30) Foreign Application Priority Data
Oct. 30, 2018 (JP) .................................. 2018-204329

(51) Int. Cl.
*G06T 7/90* (2017.01)
*G06T 7/00* (2017.01)

(52) U.S. Cl.
CPC .............. *G06T 7/90* (2017.01); *G06T 7/0012* (2013.01); *G06T 2207/10024* (2013.01); *G06T 2207/30088* (2013.01)

(58) Field of Classification Search
CPC ..................... G06T 7/90; G06T 7/0012; G06T 2207/10024; G06T 2207/30088; A61B 5/00; G01J 3/50; G01N 21/27
See application file for complete search history.

(56) References Cited

FOREIGN PATENT DOCUMENTS

| JP | 2003-275179 A | 9/2003 |
|----|---------------|--------|
| JP | 2015-023953 A | 2/2015 |

OTHER PUBLICATIONS

Lisenko, S.A. and Kugeiko, M.M., 2013. Method for determining skin pigment concentrations from multispectral images of the skin. Measurement Techniques, 56, pp. 721-729.*

(Continued)

*Primary Examiner* — Zhitong Chen
(74) *Attorney, Agent, or Firm* — ScienBiziP, P.C.

(57) ABSTRACT

A coefficient determination device determines, based on captured image data obtained by imaging a subject including one or more types of pigments, coefficients included in a function used to calculate a concentration of one desired pigment in a specific region of the subject. The coefficient determination device includes: a response calculation unit configured to calculate at least one of a first response mode indicating a relationship between a change in a component concentration of a pigment other than the desired one pigment and a change in each of the plurality of types of luminance values; and a second response mode indicating a relationship between a change in a shade intensity and a change in each of the plurality of types of luminance values;

(Continued)

and a coefficient calculation unit configured to calculate the plurality of coefficients using at least either one of the first and second response modes.

15 Claims, 6 Drawing Sheets

(56) References Cited

OTHER PUBLICATIONS

Liu, Z. and Zerubia, J., Nov. 2013. Melanin and hemoglobin identification for skin disease analysis. In 2013 2nd IAPR Asian Conference on Pattern Recognition (pp. 145-149). IEEE.*

* cited by examiner

COEFFICIENT DETERMINATION DEVICE, PIGMENT CONCENTRATION CALCULATION DEVICE, COEFFICIENT DETERMINATION METHOD, AND NON-TRANSITORY COMPUTER-READABLE STORAGE MEDIUM

TECHNICAL FIELD

The present disclosure relates to a coefficient determination device for determining a coefficient included in a function used in calculating a pigment component concentration, a pigment concentration calculation device, and the like. The present application claims priority based on Japanese Patent Application No. 2018-204329 filed in Japan on Oct. 30, 2018, the contents of which are incorporated herein by reference.

BACKGROUND ART

Conventionally, there is known a technique of calculating a pigment concentration of a skin of a subject by a calculation based on image data.

For example, PTL 1 discloses a method in which, RGB luminance values in image data are subjected to a multivariate analysis to determine magnitudes of effects of respective components of melanin, hemoglobin, and shade on the luminance values, and a melanin concentration or a hemoglobin concentration are estimated based on the determined magnitudes of the effects. In addition, there has been proposed a method of estimating the pigment concentration by performing a multiple regression analysis on the absorbance spectra of the skin and the pigment (see, for example, PTL 2).

CITATION LIST

Patent Literature

PTL 1: Japanese Unexamined Patent Application Publication No. 2003-275179 (Sep. 30, 2003).
PTL 2: Japanese Unexamined Patent Application Publication No. 2015-023953 (Feb. 5, 2015).

SUMMARY OF INVENTION

Technical Problem

However, performing a computation process such as multivariate analysis or multiple regression analysis for each image data results in a problem that a lot of processing time is required.

One of objects of the present disclosure is to realize a technique of reducing the time required for the process of calculating the pigment concentration in a specific region of a subject based on image data of the subject.

Solution to Problem

According to an aspect, the present disclosure provides a coefficient determination device configured to determine, based on captured image data obtained by imaging a subject including one or more types of pigments, a coefficient included in a function used to calculate a concentration of one desired pigment in a specific region of the subject, (i) the captured image data being data obtained by using a predetermined imaging apparatus, and having a plurality of types of luminance values representing luminances in respective wavelength bands, (ii) the function including a plurality of types of luminance values as variables and including a plurality of coefficients corresponding to the respective variables, (iii) the plurality of coefficients being obtained in association with the predetermined imaging apparatus, the coefficient determination device including a response calculation unit configured to calculate at least one of a first response mode and a second response mode, the first response mode indicating a relationship between a change in a component concentration of a pigment other than the desired one pigment and a change in each of the plurality of types of luminance values in the captured image data, and the second response mode indicating a relationship between a change in a shade intensity and a change in each of the plurality of types of luminance values in the captured image data, and a coefficient calculation unit configured to calculate the plurality of coefficients using at least either one of the first and second response modes.

According to an aspect, the present disclosure provides a coefficient determination method for determining, based on captured image data obtained by imaging a subject including one or more types of pigments, a coefficient included in a function used to calculate a concentration of one desired pigment in a specific region of the subject, (i) the captured image data being data obtained by using a predetermined imaging apparatus, and having a plurality of types of luminance values representing luminances in respective wavelength bands, (ii) the function including a plurality of types of luminance values as variables and including a plurality of coefficients corresponding to the respective variables, (iii) the plurality of coefficients being obtained in association with the predetermined imaging apparatus, the coefficient determination method including a response calculation process of calculating at least one of a first response mode and a second response mode, the first response mode indicating a relationship between a change in a component concentration of a pigment other than the desired one pigment and a change in each of the plurality of types of luminance values in the captured image data, and the second response mode indicating a relationship between a change in a shade intensity and a change in each of the plurality of types of luminance values in the captured image data, and a coefficient determination process of calculating the plurality of coefficients using at least either one of the first and second response modes.

Advantageous Effects of Invention

According to an aspect of the present disclosure, it is possible to reduce the time required for the process of calculating the pigment concentration in a specific region of a subject based on image data of the subject.

DESCRIPTION OF EMBODIMENTS

Figure 1:
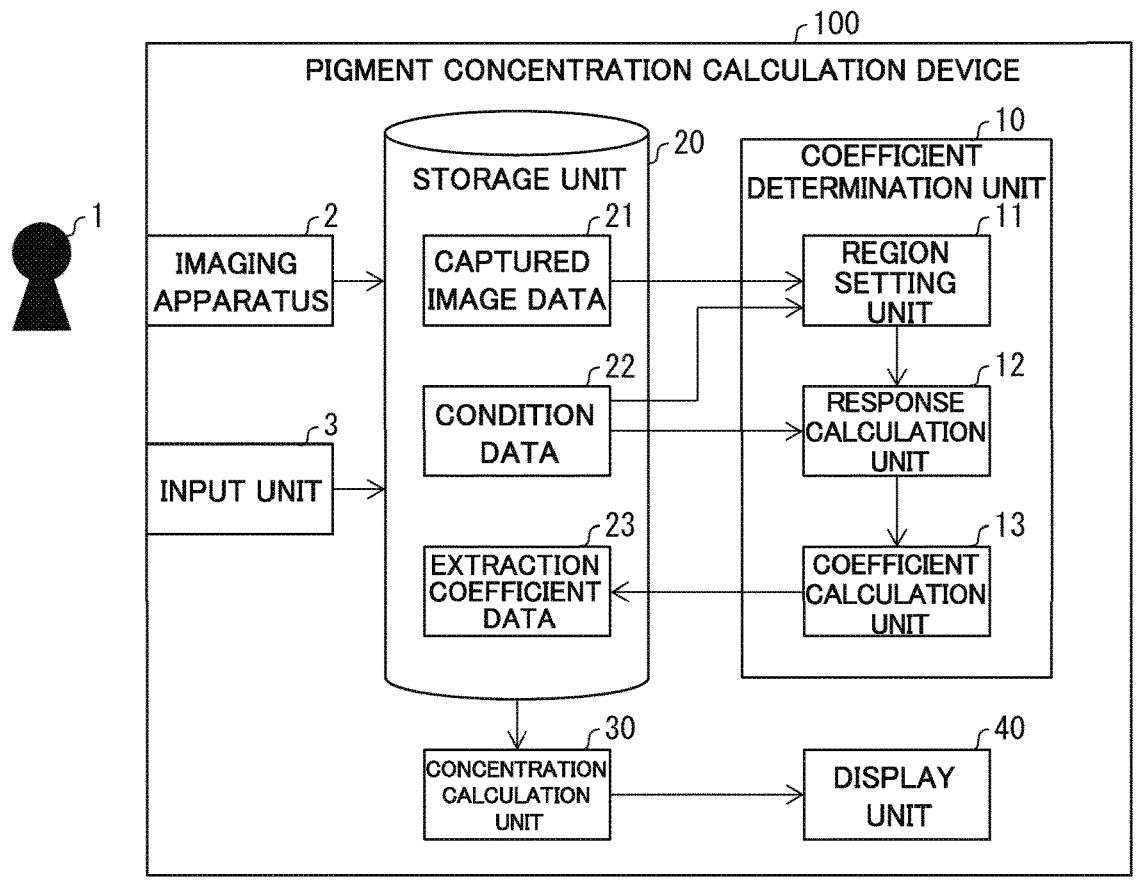
FIG. 1 is a block diagram illustrating an outline of a configuration of a pigment concentration calculation device according to Embodiment 1 of the present disclosure.

In order to facilitate the understanding of a coefficient determination device and a pigment concentration calculation device according to the present disclosure, first, a description is given on an outline of knowledge on which the present disclosure is based.

(Knowledge on which the Present Disclosure is Based)

In general, a skin color is determined by three main factors: a melanin (melanin pigment) concentration; a hemoglobin (hemoglobin pigment) concentration; and a shade intensity. Therefore, for example, if the effect of melanin and the effect of the shade intensity can be removed from the image of the skin in the image data by a computation process, the hemoglobin concentration can be calculated.

In the present description, the "shade intensity" indicates the degree to which light is attenuated by diffusion and reflection, assuming that the pigment contained in the subject does not absorb light. More details are as follows. That is, the light diffused or reflected by the subject receives various influences. When an image of a subject is captured using an imaging apparatus, the amount of light incident on the imaging apparatus depends on the position and the angle of the subject with respect to the imaging apparatus, the unevenness of the subject surface, and/or the like. That is, a reduction in the light incident on the imaging apparatus may occur due to factors such as a surface state of the subject, a positional relationship among a light source, the subject, the imaging apparatus, and other objects, and/or the like. The shade intensity indicates the magnitude of attenuation of light due to these factors. The larger the attenuation, the larger the shade intensity.

For example, in a conventional technique using a pigment component separation method, the magnitude of the effect of each component such as melanin on the luminance value is determined by performing multivariate analysis of RGB luminance values in image data, and based on the result, the pigment concentration can be estimated. In another proposed method, the pigment concentration is determined by performing multiple regression analysis on a measured skin color in terms of colors absorbed by pigments such as melanin.

However, the spectral sensitivity of each filter that generates each luminance value (for example, RGB) in the image data differs for each imaging apparatus (camera). Therefore, for example, a calculation formula f(R, G, B) for determining the hemoglobin concentration based on the luminance value may differ for each imaging apparatus. Furthermore, the calculation formula f(R, G, B) may differ depending on the concentration of melanin contained in the skin.

Therefore, in the above-described conventional technique, it is necessary to perform complicated calculations such as multivariate analysis, multiple regression analysis, or the like, for each image. This causes a problem that a long time is required to perform the process of determining the pigment concentration. Furthermore, for example, in a case where the spread of the pigment concentration distribution of the data (image) for use in multivariate analysis is small, the calculation accuracy of the pigment concentration may be low.

As a result of intensive studies, the present inventors have conceived that a mathematical formula for calculating the amount of pigment component based on each luminance value in image data is derived in advance using the spectral sensitivity of the imaging apparatus and the light absorption spectrum of the pigment. Further details are as follows. In the present description, a target pigment for which the component concentration is to be determined may be referred to as a measurement target pigment (one desired pigment), and other pigments may be referred to as non-target pigments (specific pigments).

Taking into account the spectral sensitivity of the imaging apparatus, (i) a calculation is performed to determine a response mode in which the imaging apparatus provides an output depending on a change in a component concentration of a non-target pigment, or (ii) a calculation is performed to determine a response mode in which the imaging apparatus provides an output depending on a change in a shade intensity. Then, based on the determined response mode, a relational expression (function) for calculating the component concentration of the pigment to be measured is generated in advance. The coefficient determination device according to the present disclosure is a device that performs a computation process for determining coefficients used in the above-described relational expression. The pigment concentration calculation device according to the present disclosure is a device that performs a computation process for calculating the component concentration of the measurement target pigment by using the relational expression.

Figure 2:
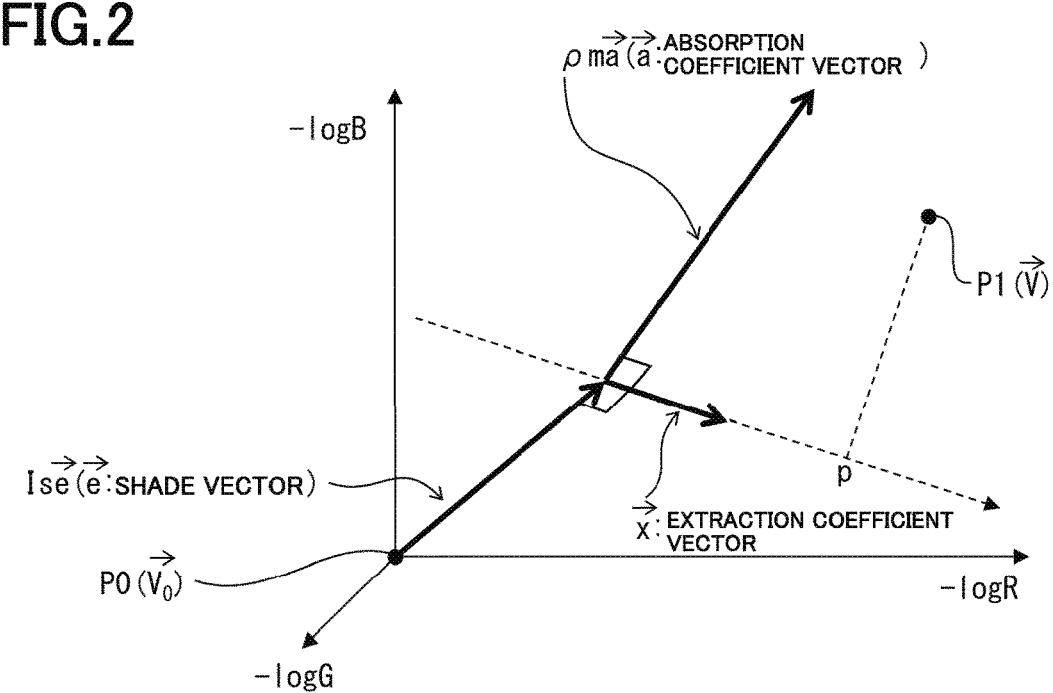
FIG. 2 is a diagram illustrating points and vectors in a three-dimensional space having coordinate axes along which logarithms of luminance values of RGB are respectively plotted, for use in illustrating an outline of knowledge on which the present disclosure is based.

Although there is no particular restriction on specific computation processes performed by the coefficient determination device and the pigment concentration calculation device, for example, the above-described computation processes may be realized by a vector operation in an orthogonal coordinate system (in a three-dimensional space) having coordinate axes along which the logarithmic values of luminance values of RGB are respectively plotted. In order to facilitate the understanding of the knowledge on which the present disclosure is based, a computation process using vectors in the three-dimensional space is schematically described below with reference to FIG. 2 for a case where a relational expression for calculating the hemoglobin concentration is generated. FIG. 2 is a diagram illustrating points and vectors in a three-dimensional space having coordinate axes along which logarithms of luminance values of RGB are respectively plotted, for use in illustrating an outline of knowledge on which the present disclosure is based.

As shown in FIG. 2, an absorption coefficient vector $a=(aR, aG, aB)$ denotes a vector representing a response mode, determined taking into account the spectral sensitivity of the imaging apparatus, in which the imaging apparatus provides an output depending on a change in the component concentration of melanin, and a shade vector $e=(eR, eG, eB)$ denotes a response mode in which the imaging apparatus provides an output depending on a change in the shade intensity. Furthermore, an extraction coefficient vector $x=(xR, xG, xB)$ denotes a vector in the above three-dimensional space for removing effects of melanin and the shade intensity. The coefficient determination device calculates this extraction coefficient vector x.

A point P0 is a point whose components are respectively given by additive inverses of logarithms of the output $V_0=(V_0R, V_0G, VB)$ provided from the imaging apparatus in a situation in which no light absorption occurs by any of melanin, hemoglobin, and shade. A point P1 is a point whose component are respectively given by additive inverses of logarithms of the output (captured image data) $V=(VR, VG, VB)$ provided by the imaging apparatus when the subject is imaged. Details of these vectors and points will be described later.

As shown in FIG. 2, a position vector $pvP1=(-\log(VR), -\log(VG), -\log(VB))$ of the point P1 is given by the linear sum of (i) the absorption coefficient vector a, (ii) the shade vector e, and (iii) a vector representing a response mode in which the imaging apparatus provides an output depending on a change in the component concentration of hemoglobin (not shown). Hereinafter, the concentration of the component of hemoglobin may be referred to as the hemoglobin concentration, and the component concentration of melanin may be referred to as the melanin concentration.

Note that the extraction coefficient vector x is a vector orthogonal to both the absorption coefficient vector a and the shade vector e. In other words, when a virtual plane is taken so as to be parallel to both the absorption coefficient vector a and the shade vector e, the extraction coefficient vector x is a vector indicating a direction of a perpendicular line perpendicular to the virtual plane. Such an extraction coefficient vector x is not uniquely determined, but if a condition is imposed, for example, such as $|x|=1$ and $xR>0$, one extraction coefficient vector x can be determined.

For the sake of simplicity, let it be assumed here that the extraction coefficient vector x is a unit vector as described above. In this case, the inner product of the position vector pvP1 of the point P1 and the extraction coefficient vector x has a value a indicating the magnitude of the component of the position vector pvP1 in the direction of the extraction coefficient vector x. This value a is equal to the sum of the inner products of respective vectors of (i) a vector corresponding to an effect of the melanin concentration (the product of the absorption coefficient vector a and the melanin concentration $\rho m$, a vector corresponding to an effect of the hemoglobin concentration, and a vector corresponding to an effect of the shade intensity (the product of the shade vector e and the shade intensity Is), respectively and (ii) the extraction coefficient vector x. Note that the value of the inner product of the absorption coefficient vector a and the extraction coefficient vector x, and the value of the inner product of the shade vector e and the extraction coefficient vector x are both equal to 0 because they are orthogonal to each other.

Therefore, a value corresponding to the hemoglobin concentration can be calculated by determining the extraction coefficient vector x in advance and by determining the inner product of the position vector pvP1 of the point P1 and the extraction coefficient vector x. Furthermore, the absolute value of the hemoglobin concentration can be also calculated by determining in advance a vector representing the response mode in which the imaging apparatus provides an output depending on a change in the hemoglobin concentration.

According to the present disclosure, as described above, without having to perform complicated calculations such as multivariate analysis for each image data, the pigment concentration calculation device is capable of obtaining a calculation result of a pigment concentration by performing a calculation of determining a linear sum which is simpler than the multiple regression process. As a result, it is possible to reduce the time required for the process of calculating the pigment concentration in a specific region of a subject based on image data. Furthermore, the pigment concentration calculation device according to the present disclosure is capable of estimating the hemoglobin concentration more accurately by performing the computation process taking into account the spectral sensitivity of the camera.

Embodiment 1

An embodiment of the present disclosure is described in detail below with reference to FIGS. 1 to 6. FIG. 1 is a block diagram illustrating an outline of a configuration of a pigment concentration calculation device 100 according to Embodiment 1. The pigment concentration calculation device 100 is a device including a coefficient determination unit (a coefficient determination device) 10 configured to determine coefficients included in a function used in calculating a pigment component concentration.

As shown in FIG. 1, the pigment concentration calculation device 100 includes an imaging apparatus 2, an input unit 3, the coefficient determination unit 10, a storage unit 20, a concentration calculation unit 30, and a display unit 40. The coefficient determination unit 10 includes a region setting unit 11, a response calculation unit 12, and a coefficient calculation unit 13. The imaging apparatus 2 images a subject 1 containing one or more types of pigments.

The pigment concentration calculation device 100 calculates the component concentration of a desired pigment based on the output from the imaging apparatus 2 and extraction coefficient data (extraction coefficient vector x). The desired pigment is one of one or more types of pigments contained in the subject 1, and more specifically, for example, the desired pigment is hemoglobin.

(Subject 1)

The subject 1 is, for example, a human body, and more specifically, a skin of the human body. The color of the skin of the human body in the captured image described below is determined by, for example, the concentrations of hemoglobin and melanin and the shade. There is no particular restriction on the subject 1, as long as it contains one or more types of pigments. In the present embodiment, the coefficient determination unit 10 calculates an extraction coefficient vector x described later in association with the subject 1.

In the following description, an example is given in which the subject 1 is a skin of a human body, the one or more types of pigments are hemoglobin and melanin, and the one desired pigment whose concentration is to be calculated is hemoglobin.

(Imaging Apparatus 2)

The imaging apparatus 2 captures an image of the subject 1 and transmits a captured image (captured image data), generated as a result of the capturing, to the storage unit 20. The imaging apparatus 2 includes, for example, an image sensor including a plurality of photo-sensitive elements each having various filters. With this configuration, the imaging apparatus 2 outputs luminance values in a plurality of wavelength bands. For example, the imaging apparatus 2 may be a common-type RGB camera or a multispectral camera. The imaging apparatus 2 captures an image of a skin of a human body and outputs luminance values in the three respective wavelength bands of R, G, and B (a plurality of wavelength bands) detected by photo-sensitive elements corresponding to respective pixels in an angle of view. The imaging apparatus 2 may be an imaging apparatus configured to capture a moving image.

(Input Unit 3)

The input unit 3 may be, for example, a combination of a mouse and a keyboard, or may be a touch panel. Using the input unit 3, a user may input various kinds of information to the pigment concentration calculation device 100. The pigment concentration calculation device 100 may be configured to include a communication unit as the input unit 3. In this case, various kinds of information are input via wired or wireless communication.

(Storage Unit 20)

The storage unit 20 is, for example, a non-volatile memory. The storage unit 20 stores captured image data 21, condition data 22, and extraction coefficient data 23.

The captured image data 21 is image data (output from the imaging apparatus 2) obtained using the imaging apparatus 2. In the present embodiment, the captured image data 21 includes RGB luminance values (a plurality of types of luminance values) representing luminance in three respective wavelength bands of R, G, and B (a plurality of wavelength bands). In the present embodiment, each pixel value in the captured image data 21 is determined by the concentrations of hemoglobin and melanin and the shade intensity of the subject 1 at a position corresponding to the pixel. In other words, in the three-dimensional space described above (see FIG. 2), the position vector representing the pixel value is given by the sum of a vector representing an effect of the hemoglobin concentration, a vector representing an effect of the melanin concentration, and a vector representing an effect of the shade intensity.

The condition data 22 is data related to various conditions used in the computation process in the pigment concentration calculation device 100. Information included in the condition data 22 will be described later in a description of each part.

The extraction coefficient data 23 is data of the extraction coefficient (the extraction coefficient vector x) calculated by the coefficient calculation unit 13 and used in the computation process by the concentration calculation unit 30 in the pigment concentration calculation device 100. The extraction coefficient is associated, at least, with the imaging apparatus 2. That is, when the imaging apparatus 2 is replaced with another one, it is necessary to correct the extraction coefficient to adapt the new imaging apparatus 2. Furthermore, it is preferable that the extraction coefficient is also associated with the type of the subject 1. The reason for this is as follows.

That is, the extraction coefficient may vary depending on the type of the subject 1. For example, when the absolute amount of hemoglobin concentration of a subject containing pigments different from those of a human skin is determined using an extraction coefficient for use in calculating a hemoglobin concentration of the human skin, the resultant determined value may have a large error from a real value.

However, for example, in a case where relative values of the hemoglobin concentration are determined for the same subject, it may be possible to obtain information indicating a significant difference in relative values of the hemoglobin concentration. This makes it possible, for example, to measure a pulse wave (see Embodiment 3 described later).

There is no particular restriction on the type of the subject 1 that is to be associated with the extraction coefficient, and the type may be appropriately set in advance. For example, the type of the subject 1 may be set according to a difference in a skin color (for example, three types of skin colors including a fair skin, a standard skin, and a dark skin may be set).

(Region Setting Unit 11)

The region setting unit 11 in the coefficient determination unit 10 sets a specific region of the subject 1 based on the captured image data 21. For example, the specific region may be one pixel or another specific region (a region of interest). The region of interest may be, for example, an entire face, a palm of a hand, or the like. In the setting of the region of interest, for example, a representative value of the set region of interest (for example, an average value of pixel values in the region of interest) can be used.

An example is described below for a case where a certain pixel is set as a specific region. The region setting unit 11 may set such a specific region according to the condition data 22.

(Response Calculation Unit 12)

Figure 3:
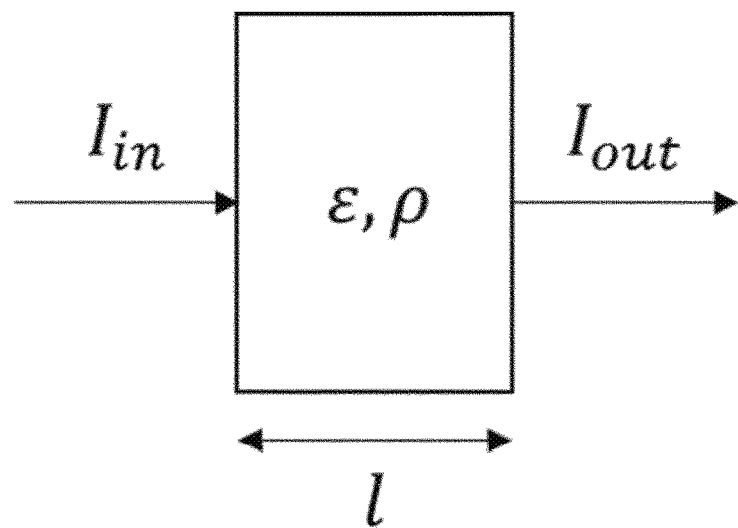
FIG. 3 is a schematic diagram for illustrating a relational expression for a case where light is absorbed by a substance.
Figure 4:
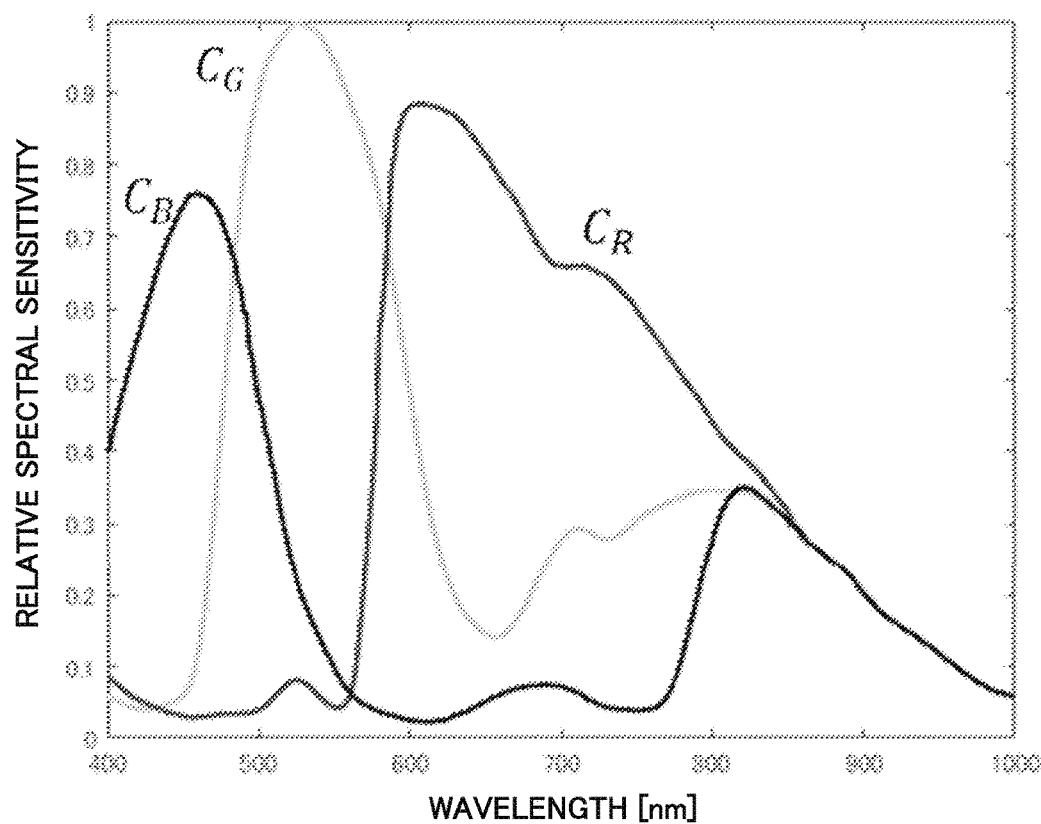
FIG. 4 is a diagram illustrating a spectral sensitivity of an imaging apparatus.

A process executed by the response calculation unit 12 is described below with reference to FIGS. 3 to 5. FIG. 3 is a schematic diagram for explaining a relational expression in a situation in which light is absorbed by a substance. FIG. 4 is a diagram illustrating a spectral sensitivity of the imaging apparatus 2.

As shown in FIG. 3, when the absorption coefficient of a certain substance is $\varepsilon$, the concentration is $\rho$, and the distance by which light passes through the substance is 1, then the relation between the intensity of light $I_{in}$ incident on the substance and the intensity of light $I_{out}$ emerging after passing through the substance is given as follows. That is, according to the Lambert-Beer's law, the relation is expressed as $-\log(I_{out}/I_{in}) = \varepsilon\rho l$. Applying this relational expression to light of each wavelength yields $I_{out}(\lambda) = I_{in}(\lambda) 10^{\wedge}(-\varepsilon(\lambda)\rho l)$.

As shown in FIG. 4, the sensitivity of the detection element of the imaging apparatus 2 in the three wavelength bands of R, G, and B changes depending on the wavelength. Let it be assumed here that the spectral sensitivities of R, G, and B of the imaging apparatus 2 are respectively given by $C_R(\lambda)$, $C_G(\lambda)$, and $C_B(\lambda)$. An example is described below for a case where a calculation is performed as to an absorption coefficient vector a (a first response mode) representing a relationship between a change in the melanin concentration and a change in the luminance value of the captured image data 21 in the three-dimensional space described above (see FIG. 2).

When light $I_{out}(\lambda)$, emerging from the subject 1 after receiving an influence of only absorption by melanin, is captured by the imaging apparatus 2 (the camera), a camera output V={VR, VG, VB} for a certain pixel can be virtually determined as follows. That is, VR is given by a value obtained by integrating, over all wavelengths, a spectrum which is obtained as a result of multiplying the light $I_{out}(\lambda)$ emerging from the subject 1 by $C_R(\lambda)$ at each wavelength. VG is obtained in a similar manner to the VR described above except that $C_G(\lambda)$ is multiplied, and VB is obtained in a similar manner to the VR except that $C_B(\lambda)$ is multiplied. In the actual calculation, the wavelengths are given as discrete values, and the integral is given by the sum for the respective discrete wavelength values. Note that the spectral sensitivities $C_R(\lambda)$, $C_G(\lambda)$, and $C_B(\lambda)$ are given taking into account the transmittance of each filter, the transmittance of the lens of the camera, and the like.

Herein it is assumed that the incident light $I_{in}(\lambda)$ is light (white light) with intensity that is constant regardless of the wavelength. In this case, $I_{in}(\lambda)=1$. The distance 1 through which light passes may be equal to 1 (a unit length), or vary depending on the wavelength.

The relationship between the melanin concentration ρm and the camera output V={VR, VG, VB} is expressed by the following formula (1). Note that in formula (1), individual formulas in terms of R, G, and B are combined into a single formula.

[Math 1]

$$\left\{ VR \text{ or } VG \text{ or } VB \right\} = \int I_{in(\lambda)} 10^{-\varepsilon(\lambda)\rho l} C_{R \text{ or } G \text{ or } B(\lambda)} d\lambda \\ = \sum_i I_{in(\lambda_i)} 10^{-\varepsilon(\lambda_i)\rho l} C_{R \text{ or } G \text{ or } B(\lambda_i)} \Delta\lambda \quad (1)$$

In this formula, ρ is the melanin concentration ρm, and ε(λ) is the light absorption spectrum of melanin.

Figure 5A:
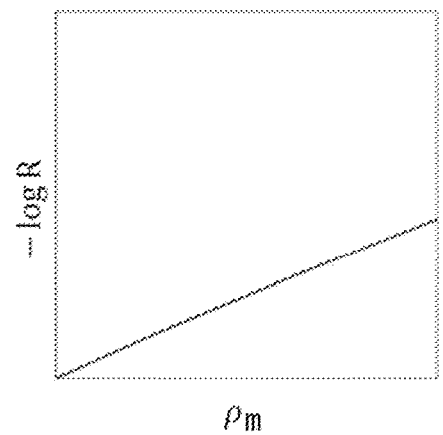
FIG. 5A is a diagram illustrating a relationship between a melanin concentration and an output of R from an imaging apparatus.
Figure 5B:
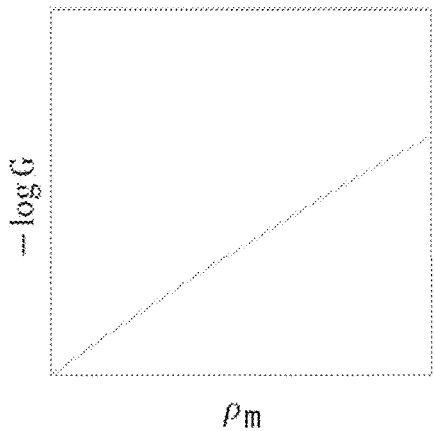
FIG. 5B is a diagram illustrating a relationship between a melanin concentration and an output of G from an imaging apparatus.
Figure 5C:
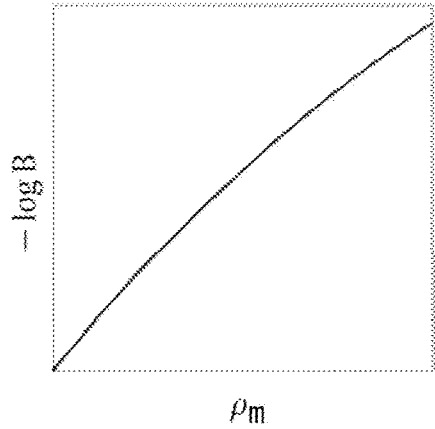
FIG. 5C is a diagram illustrating a relationship between a melanin concentration and an output of B from an imaging apparatus.

Based on formula (1) described above, the response calculation unit 12 determines the response mode in which the camera provides the output V={VR, VG, VB} depending on a change in the melanin concentration ρm. The light absorption spectrum ε(λ) of melanin may be obtained experimentally in advance, or a known spectrum may be used. FIG. 5 is a diagram representing a relationship between the melanin concentration ρm and the camera output V, and more specifically, FIG. 5A represents an output value of R, FIG. 5B represents an output value of G, and FIG. 5C represents an output value of B. In these figures, the melanin concentration ρm is plotted along a horizontal axis, and the additive inverse of the logarithm of the camera output V, that is, −log(V), is plotted along a vertical axis.

As can be seen from FIGS. 5A to 5C, the relationship between the melanin concentration ρm and the camera output V can be approximately expressed by formula (2) shown below.

[Math 2]

$$\left\{ \begin{array}{l} -\log R = a_R \rho_m \\ -\log G = a_G \rho_m \\ -\log B = a_B \rho_m \end{array} \right\} \quad (2)$$

More specifically, for example, the relationship between the melanin concentration ρm and the output value of R may pass through the origin as shown in FIG. 5A, or may intercept on the vertical axis as in the form such as −log (R)=aRρm+bR. When normalization is performed such that the output value of R has a value of R=1 (a maximum value) when ρm=0, the intercept bR=0 and thus the relationship has the form given in formula (2) described above.

The response calculation unit 12 employs a vector a=(aR, aG, aB) obtained in the above-described manner as the melanin absorption coefficient vector a. Alternatively, the response calculation unit 12 may normalize the vector such that a=(aR, aG, aB)/√(aR²+aG²+aB²) and may employ the resultant normalized vector as the absorption coefficient vector a.

For example, in the case where the relationship between the melanin concentration ρm and the output value of R is virtually determined in the above-described manner, effects of factors other than melanin are incorporated into the term of bR in the above-described formula. Therefore, when absorption by a pigment such as hemoglobin has an influence (on an actual camera output), no significant change occurs in the absorption coefficient vector a=(aR, aG, aB).

The determination of the relationship between the melanin concentration ρm and each of the output values of RGB is not limited to the determination by the calculation such as that described above. Alternatively, the relationship may be experimentally determined.

Furthermore, the response calculation unit 12 determines a shade vector e (a second response mode) indicating a relationship between a change in the luminance value of the captured image data 21 and a change in the shade intensity Is of the subject 1, in the above-described three-dimensional space (see FIG. 2). The response calculation unit 12 determines the shade vector e, for example, such that e=(1, 1, 1). This shade vector e may be determined experimentally or determined by a calculation and a simulation. The shade vector e may be stored in the storage unit 20 as the condition data 22.

More specifically, in a similar manner to the above-described case in which the absorption coefficient vector a of melanin is determined according to formula (1), the shade vector e may be determined by determining the response mode of the camera output V={VR, VG, VB} depending on a change in the shade intensity Is. For example, the relationship between the shade intensity Is and the camera output V={VR, VG, VB} is expressed by formula (3) shown below. Note that in formula (3), individual formulas in terms of R, G, and B are combined into a single formula.

[Math 3]

$$\{VR \text{ or } VG \text{ or } VB\} = \int I_{in(\lambda)} 10^{-I_s} C_{R \text{ or } G \text{ or } B(\lambda)} d\lambda \quad (3)$$

In a similar manner to the above-described case of the relationship between the melanin concentration ρm and the camera output V, the relationship between the shade intensity Is and the camera output V may be approximately represented by a formula (4) shown below.

[Math 4]

$$\left\{ \begin{array}{l} -\log R = e_R I_s \\ -\log G = e_G I_s \\ -\log B = e_B I_s \end{array} \right\} \quad (4)$$

The vector e=(eR, eG, eB) obtained according to formula (4) described above may be employed as the shade vector e.

(Coefficient Calculation Unit 13)

A process executed by the coefficient calculation unit 13 is described below with reference to FIG. 2. As shown in FIG. 2, a position vector is given as described below for a point P1 (corresponding to the output V) in an orthogonal coordinate system (a three-dimensional space) in which the logarithm of each luminance value of RGB is plotted along a corresponding one of coordinate axes of the orthogonal coordinate system. That is, the position vector of the point P1 is given by the sum of the following vectors: a vector obtained as a result of multiplying the absorption coefficient vector a by the melanin concentration ρm; a vector obtained as a result of multiplying the shade vector e by the shade intensity Is; and a vector obtained as a result of multiplying the hemoglobin concentration ρh by a vector indicating a response mode in which the imaging apparatus provides an output depending on a change in the component concentration of hemoglobin. That is, the position vector of the point P1 can be expressed by formula (5) shown below.

[Math 5]

$$-\log \vec{V} = -\log \vec{V}_0 + \vec{a}\rho_m + \vec{b}\rho_h + \vec{e}I_s \quad (5)$$

In this formula, $V_0$ is a vector indicating the camera output in a case where there is no absorption by melanin, hemoglobin, and shade, a is an absorption coefficient vector of melanin calculated by the response calculation unit 12, e is a shade vector determined by the response calculation unit 12, and b is a vector indicating a response mode in which the imaging apparatus provides an output depending on a change in the hemoglobin concentration ρh.

The coefficient calculation unit 13 calculates a vector orthogonal to both the absorption coefficient vector a of melanin and the shade vector e, and employs the resultant vector as the extraction coefficient vector x used in extracting the hemoglobin concentration. The vector x=(xR, xG, xB) is not uniquely determined, but any arbitrary vector satisfying the condition that it is orthogonal to both the absorption coefficient vector a and the shade vector e may be the extraction coefficient vector x. Actually, a condition such as |x|=1 and xR>0 may be imposed, and, under this condition, the calculation may be performed.

The coefficient calculation unit 13 calculates extraction coefficients, as the extraction coefficient vector x, specific to the imaging apparatus 2. The resultant calculated extraction coefficient vector x is stored, for example, in the storage unit 20 as the extraction coefficient data 23.

(Concentration Calculation Unit 30)

For the image data acquired using the imaging apparatus 2, the concentration calculation unit 30 acquires the extraction coefficients associated with the imaging apparatus 2 from the extraction coefficient data 23. Using the acquired extraction coefficients, it is possible to estimate the hemoglobin concentration.

More specifically, the inner product of the additive inverse of the logarithm of the camera output, −log(V), and the extraction coefficient vector x=(xR, xG, xB) is expressed by formula (6) shown below.

[Math 6]

$$-\log \vec{V} \cdot \vec{x} = (-\log \vec{V}_0 + \vec{a}\rho_m + \vec{b}\rho_h + \vec{e}I_s) \cdot \vec{x} \\ = -\log \vec{V}_0 \cdot \vec{x} + \rho_h(\vec{b} \cdot \vec{x}) \quad (6)$$

Here, the inner product of the absorption coefficient vector a of melanin and the extraction coefficient vector x, and the inner produce of the shade vector e of and the extraction coefficient vector x are both equal to 0.

In the above formula, since the absorption coefficient vector $-\log(V_0) \cdot x$ and b·x are constants, $-\log(V) \cdot x$ has a value corresponding to the hemoglobin concentration ρh. Therefore, by calculating $-\log(V) \cdot x = xR\log(VR) + xG\log(VG) + xB\log(VB)$, it is possible to obtain a value proportional to the hemoglobin concentration ρh, and thus, based on this value, it is possible to estimate the hemoglobin concentration ρh.

Note that formula (7) shown below can be obtained by modifying the above-described formula.

[Math 7]

$$\rho_h = \frac{1}{\vec{b} \cdot \vec{x}} \log \frac{\vec{V}_0 \cdot \vec{x}}{\vec{V} \cdot \vec{x}} \quad (7)$$

Using this formula, the concentration calculation unit 30 can also calculate the absolute amount of the hemoglobin concentration ρh. In this case, it is necessary to determine the absorption coefficient vector b of hemoglobin in advance. The absorption coefficient vector b of hemoglobin can be determined in a similar manner to the determining of the absorption coefficient vector a of melanin. For example, the concentration calculation unit 30 or the response calculation unit 12 may calculate the absorption coefficient vector b of hemoglobin.

(Display Unit 40)

The display unit 40 is an apparatus capable of displaying an image, and displays a value corresponding to the hemoglobin concentration ρh calculated by the concentration calculation unit 30 or the absolute amount of the hemoglobin concentration ρh.

(Processing Flow)

Figure 6:
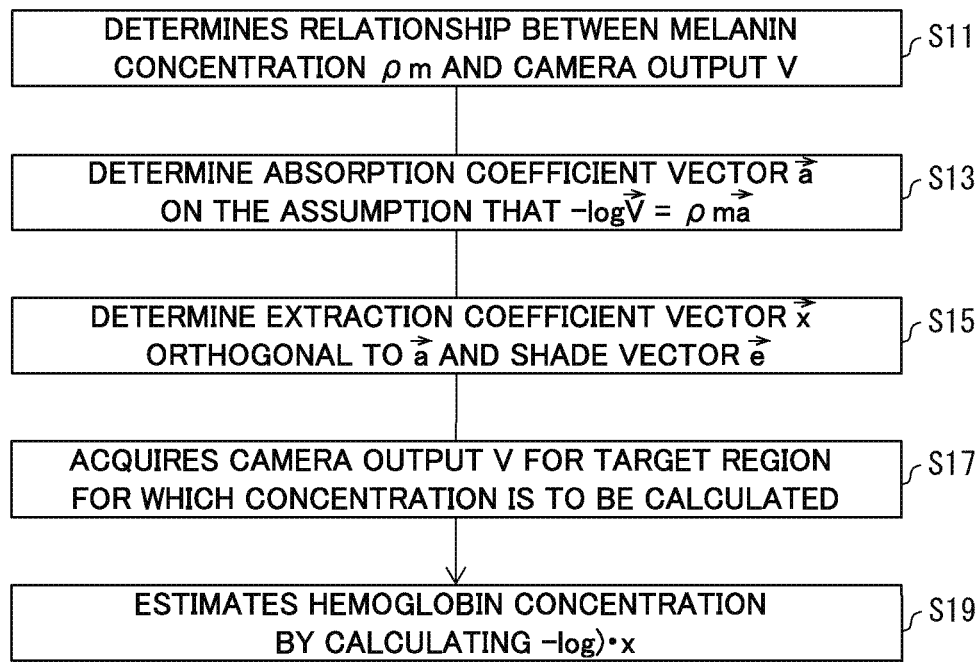
FIG. 6 is a flowchart illustrating an example of an overall flow of a process executed by a pigment concentration calculation device according to Embodiment 1 of the present disclosure.

Next, an example of a flow of a process (an information processing method) of calculating the hemoglobin concentration ρh using the pigment concentration calculation device 100 is described below with reference to FIG. 6. FIG. 6 is a flowchart illustrating an example of an overall flow of a process executed by the pigment concentration calculation device 100. It is assumed that an RGB camera is used as the imaging apparatus 2, and the subject 1 is a skin of a human body.

As shown in FIG. 6, first, the response calculation unit 12 determines the relationship between the melanin concentration ρm and the camera output V (see FIGS. 5A to 5C) for a specific region, set by the region setting unit 11, in the captured image data 21 (S11). Next, the response calculation unit 12 calculates the absorption coefficient vector a on the assumption that $-\log(V) = \rho ma$ (where V and a are vectors) from the relationship obtained in S11 (S13: response calculation process). The response calculation unit 12 also determines the shade vector e.

Next, the coefficient calculation unit 13 calculates the extraction coefficient vector x orthogonal to the absorption coefficient vector a and the shade vector e obtained in S13

(S15: coefficient calculation process). The calculated extraction coefficient vector x is stored as the extraction coefficient data 23 in the storage unit 20 in association with the specific imaging apparatus 2.

The concentration calculation unit 30 acquires captured image data 21 (a camera output V) of a target for which the hemoglobin concentration ρh is to be calculated (S17). For the acquired captured image data 21, the extraction coefficient vector x associated with the imaging apparatus 2 by which the image data 21 was captured is acquired from the extraction coefficient data 23. The concentration calculation unit 30 estimates the hemoglobin concentration ρh by calculating −log (V)·x (S19).

Advantageous Effects

In the pigment concentration calculation device 100 according to the present embodiment, the coefficient determination unit 10 determines the response mode (the melanin absorption coefficient vector a) in which the camera output is provided in response to the melanin concentration based on the light absorption spectrum of melanin and the spectral sensitivity of the camera. The coefficient determination unit 10 also determines the response mode (the shade vector e) in which the camera output is provided in response to the shade intensity based on the spectral sensitivity of the camera.

The coefficient determination unit 10 calculates in advance the extraction coefficients in the form of the extraction coefficient vector x for use in extracting the component concentration of one target pigment (for example, hemoglobin). The extraction coefficient vector x can be calculated by determining a vector orthogonal to both the absorption coefficient vector a of melanin and the shade vector e. The coefficient determination unit 10 can obtain a camera-specific extraction coefficient vector x.

The concentration calculation unit 30 can evaluate the hemoglobin concentration ρh at each pixel, for example, by calculating −log(V)·x for the camera output V at the pixel of the captured image data 21. When a region of interest in the captured image data 21 is specified, and the camera output V is given by the sum or the average of camera output values in the specified region of interest, the concentration calculation unit 30 can estimate the hemoglobin concentration ρh in the specified region of interest.

As described above, the pigment concentration calculation device 100 does not need to perform complicated calculations such as multiple regression analysis, multivariate analysis, or the like, for each image. Instead, it is sufficient for the pigment concentration calculation device 100 to calculate in advance the extraction coefficient vector x specific to the imaging apparatus 2. In addition, the hemoglobin concentration ρh can be evaluated by calculating the linear sum, which is a relatively simple calculation. Therefore, it is possible to reduce the time required to perform the process of calculating the pigment concentration in a specific region of the subject 1 based on the captured image data 21 of the subject 1.

Furthermore, since the calculation is performed using the same calculation formula for different images or different detection target regions, the accuracy of the calculation of the hemoglobin concentration ρh does not change depending on the quality of the captured image data 21. The coefficient determination unit 10 uses the spectral sensitivity of the camera. This makes it possible to calculate the hemoglobin concentration ρh with higher accuracy and precision.

(Notes)

In the embodiment described above, the pigment concentration calculation device 100 configured to perform the process has been described assuming that the incident light $I_{in}(\lambda)$ is light (white light) with intensity that is constant regardless of the wavelength. In practice, the ambient light or the illumination light used in imaging the subject 1 may have a spectral intensity distribution in which the spectral intensity changes as a function of the wavelength. In a case where the incident light $I_{in}(\lambda)$ has a spectral intensity distribution in which the spectral intensity does not extremely change depending on the wavelength, a change in the spectral distribution of the incident light $I_{in}(\lambda)$ results in an effect such that the entire right side in the formula (1) described above is multiplied by a constant. Therefore, when the formula −log(R)=aRρm+bR is determined, a change in the imaging environment is incorporated in bR. Therefore, no significant change occurs in the value of the absorption coefficient vector a. As a result, the extraction coefficient vector x calculated in the above-described manner using the absorption coefficient vector a obtained assuming that white light is used as the incident light $I_{in}(\lambda)$ is robust, to a certain degree, to a change in the imaging environment. The pigment concentration calculation device 100 can easily estimate the component concentration of the pigment by using the extraction coefficient vector x obtained in the above-described manner, although a small error may occur due to a change in the imaging environment.

(Modifications)

Modifications of the pigment concentration calculation device 100 according to the present embodiment are described below.

(a) In a pigment concentration calculation device according to a modification of the present disclosure, for example, a subject 1 containing, for example, three types of pigments may be imaged by using, for example, an RGB camera as the imaging apparatus 2, and the concentration of a desired one of the three pigments may be estimated. In this case, the coefficient determination unit 10 may calculate the extraction coefficient based on the response mode in which the camera output is provided depending on a change in the concentration of each of the remaining two pigments.

For example, the three pigments may be melanin, hemoglobin, and carotene. Based on the response modes in which the camera outputs in terms of melanin and carotene are provided, the extraction coefficient for hemoglobin can be calculated.

Note that the subject is not limited to a skin of a human body. For other subjects containing a plurality of types of pigments, the concentration of a particular pigment can be calculated by using the pigment concentration calculation device according to one aspect of the present disclosure.

(b) In a pigment concentration calculation device according to another modification of the present disclosure, in a case where an imaging apparatus used is capable of outputting luminance values in two wavelength bands, an extraction coefficient can be determined based on a response mode in which the imaging apparatus provides an output depending on a change in a concentration of one pigment. It is also possible to determine the extraction coefficients based on a response mode in which the imaging apparatus provides an output depending on a change in the shade intensity.

(c) In the pigment concentration calculation device according to one modification of the present disclosure, the imaging apparatus 2 may output luminance values in many wavelength bands, for example, as a spectroscope or a hyperspectral camera. In this case, the information output from the imaging apparatus 2 may not include information regarding a spatial distribution of luminance values. The pigment concentration calculation device can calculate a luminance value in each of three wavelength bands of, for example, R, G, and B, based on luminance values in many wavelength bands output from the imaging apparatus 2, and can perform various processes using the calculated luminance values.

(d) In the pigment concentration calculation device 100 according to Embodiment 1 described above, it has been assumed that the incident light $I_{in}(\lambda)$ is light (white light) with intensity that is constant regardless of the wavelength. In contrast, in a pigment concentration calculation device according to one modification of the present disclosure, the incident light $I_{in}(\lambda)$ may be ambient light actually used in imaging the subject 1, or spectral information on the illumination light may be used.

A slight change may occur in the absorption coefficient vector a depending on a condition (an incident light spectrum $I_{in}(\lambda)$) of the ambient light used in the imaging. In one modification of the present disclosure, the pigment concentration calculation device determines the extraction coefficient vector x specific not only to the imaging apparatus 2 but also to a condition of an imaging environment. This makes it possible to estimate the pigment concentration more accurately.

(e) The coefficient calculation unit 13 may calculate the extraction coefficient vector x in advance so as to vary depending on a specific melanin concentration range in which the hemoglobin concentration in the captured image data 21 is to be measured. That is, the extraction coefficient vector x is calculated so as to have a value specific to the imaging apparatus 2 and also specific to, for example, each predetermined range of the melanin concentration. For example, the concentration calculation unit 30 may use an extraction coefficient vector x determined depending on a skin color of a human body such that the extraction coefficient vector x is suitable for the skin color, which makes it possible to estimate the pigment concentration more accurately.

(f) The coefficient calculation unit 13 determines the extraction coefficient vector x based on a response mode in which the imaging apparatus provides an output depending on a change in the concentration of a pigment component, or a response mode in which the imaging apparatus provides an output depending on a change in the shade intensity, or based on both the response mode in which the imaging apparatus provides the output depending on the change in the concentration of the pigment component and the response mode in which the imaging apparatus provides the output depending on the change in the shade intensity. Each response mode may be determined experimentally or may be determined by a theoretical calculation.

(g) The number of types of luminance values output from the imaging apparatus may be larger than three (for example, R, G, and B). The pigment concentration calculation device according to one aspect of the present disclosure is capable of calculating the concentration of one desired pigment component by using captured image data obtained by imaging a subject containing a plurality of types of pigments (for example, four or more types of pigments). For example, in a case where a subject containing nine types of pigments is imaged using an imaging apparatus capable of outputting luminance values in ten wavelength bands, it is possible to calculate extraction coefficients corresponding to the imaging apparatus (and the subject) by using a response mode (for example, an absorption coefficient vector in a 10-dimensional vector space) in which the imaging apparatus provides an output depending on a change in a concentration of each of eight pigments (non-target pigments) other than the one desired pigment, and a response mode (for example, an shade vector in the 10-dimensional vector space) in which the imaging apparatus provides an output depending on a change in a shade intensity. In this case, for example, an extraction coefficient vector is given by a vector which is orthogonal, in the 10-dimensional vector space, to all nine vectors indicating the response modes.

For example, in a case where a subject containing ten types of pigments is imaged using an imaging apparatus capable of outputting luminance values in ten wavelength bands, it is possible to calculate extraction coefficients depending on the imaging apparatus by using a response mode (for example, an absorption coefficient vector in a 10-dimensional vector space) in which the imaging apparatus provides an output depending on a change in a concentration of each of nine pigments (non-target pigments) other than one desired pigment.

Note that it is not necessary to use information of all wavelength bands that can be output by the imaging apparatus. For example, when the subject is a skin of a human body, it is possible to calculate an extraction coefficient for use in calculating a hemoglobin concentration by using outputs in three wavelength bands out of ten wavelength bands that can be output by the imaging apparatus based on a response mode in which the imaging apparatus provides an output depending on a change in a melanin concentration, and a response mode in which the imaging apparatus provides an output depending on a change in a shade intensity.

In summary, the pigment concentration calculation device according to one aspect of the present disclosure is capable of determining an extraction coefficient a response mode in which the imaging apparatus responds to a change in a concentration of each of a plurality of types of pigments, and a response mode in which the imaging apparatus responds to a change in a shade intensity. Note that the pigment concentration calculation device may not use the response mode in which the imaging apparatus responds to the change in the shade intensity. In this case, the extraction coefficient may be determined based on the response mode in which the imaging apparatus responds to the change in each of the one or more non-target pigments.

However, it is necessary that the sum of respond modes used in determining the extraction coefficient, that is, the sum of (i) the number of response modes (for example, the number of absorption coefficient vectors) in which the imaging apparatus responds to changes in concentrations of respective non-target pigments, and (ii) the number of response modes (for example, the number of shade vectors) in which the imaging apparatus responds to a change in the shade intensity, is smaller than the number of outputs of the imaging apparatus 2 (for example, the number of types of luminance values capable of being output).

Sub-Summary

According to one aspect of the present disclosure, as described above, there is provided the coefficient determination device (a coefficient determination unit 10) configured to determine, based on captured image data obtained by imaging a subject 1 including one or more types of pigments, coefficients included in a function used to calculate a concentration of one desired pigment (hemoglobin) in a specific region of the subject 1, (i) the captured image data being data obtained by using a predetermined imaging apparatus 2, and having a plurality of types of luminance values (R, G, B) representing luminances in respective wavelength bands, (ii) the function including a plurality of types of luminance values as variables and including a plurality of coefficients corresponding to the respective variables, (iii) the plurality of coefficients being obtained in association with the predetermined imaging apparatus 2, the coefficient determination device including: a response calculation unit 12 configured to calculate at least one of following response modes: a first response mode (an absorption coefficient vector a of melanin) indicating a relationship between a change in a component concentration of a pigment (melanin) other than the desired one pigment and a change in each of the plurality of types of luminance values in the captured image data; and a second response mode (a shade vector e) indicating a relationship between a change in a shade intensity and a change in each of the plurality of types of luminance values in the captured image data; and the coefficient calculation unit 13 configured to calculate the plurality of coefficients using at least either one of the first and second response modes.

The second response mode is represented as a shade vector including parameters as components respectively indicating degrees of changes in additive inverses of logarithms of the plurality of types of luminance values caused by a change in the shade intensity.

The first response mode is represented such that in a case where, for a certain pigment other than the desired one pigment, the degree of change in the additive inverse of the logarithm of each of the plurality of types of luminance values caused by the change in the component concentration of the certain pigment is approximately expressed by a linear function, the first response mode is represented by an absorption coefficient vector including components given by proportional coefficients in the respective linear functions.

The coefficient calculation unit 13 calculates the plurality of coefficients such that the coefficients are given by respective components of an extraction coefficient vector x orthogonal at least to one of the shade vector and the absorption coefficient vector associated with a pigment other than the desired one pigment.

The pigment concentration calculation device 100 includes the concentration calculation unit 30 configured to calculate the concentration of the desired one pigment in the specific region of the subject 1 in the captured image data acquired from the predetermined imaging apparatus 2, by using the coefficient determination device (the coefficient determination unit 10) and using the coefficients determined by the coefficient determination device, and based on the product of the coefficients and the additive inverses of logarithms of the plurality of types of luminance values.

According to an aspect, the present disclosure provides a coefficient determination method for determining, based on captured image data obtained by imaging a subject including one or more types of pigments, coefficients included in a function used to calculate a concentration of one desired pigment in a specific region of the subject, (i) the captured image data being data obtained by using a predetermined imaging apparatus, and having a plurality of types of luminance values representing luminances in respective wavelength bands, (ii) the function including a plurality of types of luminance values as variables and including a plurality of coefficients corresponding to the respective variables, (iii) the plurality of coefficients being obtained in association with the predetermined imaging apparatus, the coefficient determination method including a response calculation process of calculating at least one of following response modes: a first response mode indicating a relationship between a change in a component concentration of a pigment other than the desired one pigment and a change in each of the plurality of types of luminance values in the captured image data; and a second response mode indicating a relationship between a change in a shade intensity and a change in each of the plurality of types of luminance values in the captured image data; and a coefficient determination process of calculating the plurality of coefficients using at least either one of the first and second response modes.

Embodiment 2

Another embodiment of the present disclosure is described below. For convenience of explanation, same reference symbols are used to denote elements having same functions as those of elements which have been described in the previous embodiment, and further duplicated explanations thereof are omitted.

In Embodiment 1 described above, the response calculation unit 12 determines the absorption coefficient vector a of melanin by performing linear regression as described with reference to FIGS. 5A to 5C. In contrast, the pigment concentration calculation device according to Embodiment 2 is different from that according to Embodiment 1 in that the response calculation unit 12 determines the absorption coefficient vector a by determining slopes from tangent lines of graphs shown in FIGS. 5A to 5C.

Figure 7:
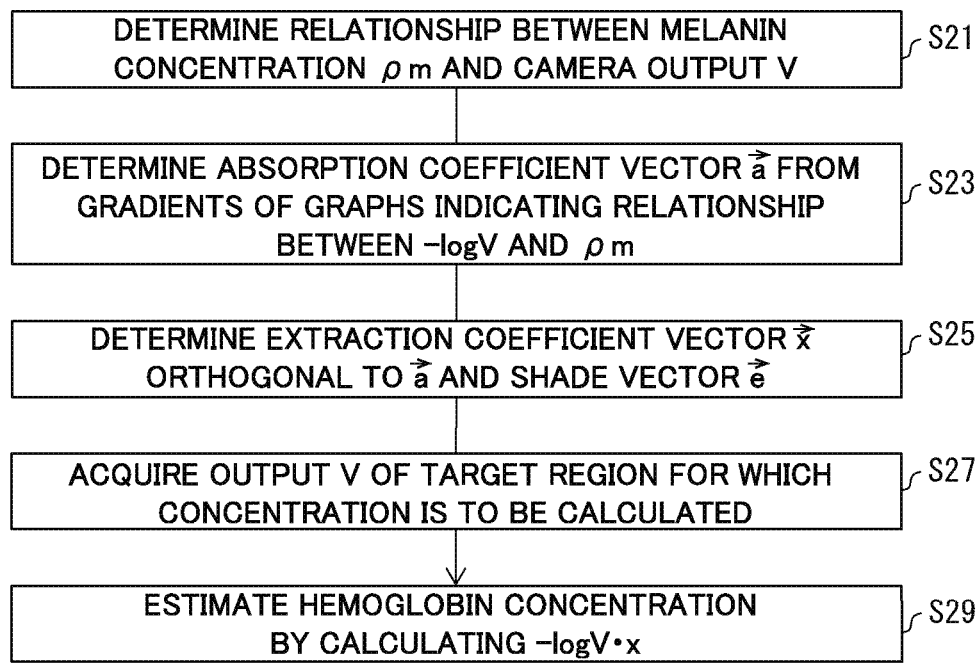
FIG. 7 is a flowchart illustrating an example of an overall flow of a process executed by a pigment concentration calculation device according to Embodiment 2 of the present disclosure.

FIG. 7 is a flowchart illustrating an example of an overall flow of a process executed by the pigment concentration calculation device according to the present embodiment. As shown in FIG. 7, first, based on a light absorption spectrum of melanin $\varepsilon(\lambda)$ and spectral sensitivities $C_R(\lambda)$, $C_G(\lambda)$, and $C_B(\lambda)$ of a camera, the response calculation unit 12 determines the relationship between the melanin concentration $\rho m$ and the camera output V={VR, VG, VB} (see FIGS. 5A to 5C) for a specific region, set by the region setting unit 11, in the captured image data 21 (S21).

Next, the response calculation unit 12 estimates the melanin concentration $\rho m$ of a skin for which the hemoglobin concentration $\rho h$ is to be estimated, and the response calculation unit 12 employs the resultant melanin concentration as an estimated melanin concentration $\rho m0$. Then, from the relationship obtained in S21, the differentiation of the additive inverse of the logarithm of the camera output $-\log(V)$ at $\rho m = \rho m0$ is employed as the absorption coefficient vector a (S23). The response calculation unit 12 also determines the shade vector e.

Figure 8A:
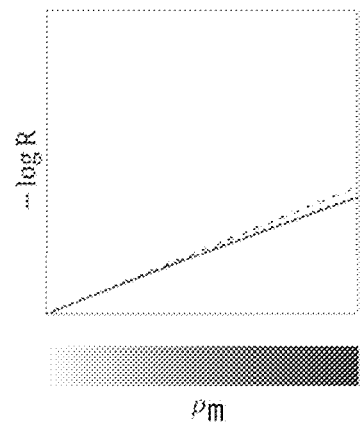
FIG. 8A is a diagram illustrating output values of R for use in explaining a relationship between a melanin concentration and an output from an imaging apparatus, and a tangent line of a graph.
Figure 8B:
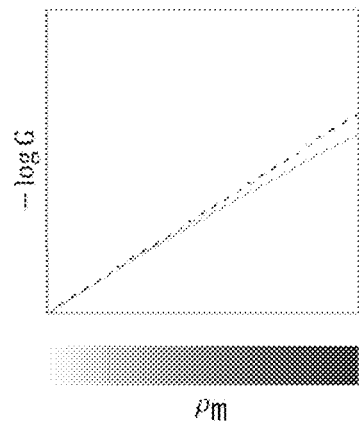
FIG. 8B is a diagram illustrating output values of G for use in explaining a relationship between a melanin concentration and an output from an imaging apparatus, and a tangent line of a graph.
Figure 8C:
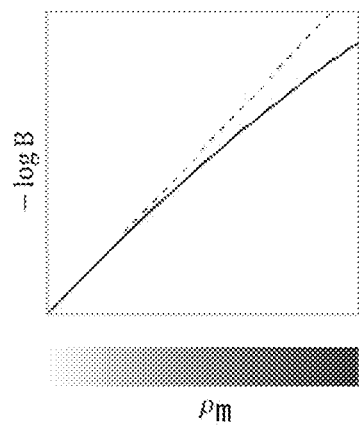
FIG. 8C is a diagram illustrating output values of B for use in explaining a relationship between a melanin concentration and an output from an imaging apparatus, and a tangent line of a graph.

An example of the absorption coefficient vector a according to the present embodiment is described below with reference to FIGS. 8A to 8C. FIG. 8 is a diagram illustrating relationships between the melanin concentration $\rho m$ and the output from the imaging apparatus, and also illustrating tangent lines of graphs, and more specifically, FIG. 8A shows an output value of R, FIG. 8B shows an output value of G, and FIG. 8C shows an output value of B. Dotted lines represent tangent lines at $\rho m = \rho m0$. Color bars at the bottoms of the graphs represent colors captured by the imaging apparatus 2 corresponding to the melanin concentration $\rho m$.

As shown in FIGS. 8A to 8C, the slope of each graph varies slightly depending on the melanin concentration $\rho m$. This means that, for example, the absorption coefficient vector a of melanin slightly varies depending on a difference in skin color caused by a difference in the amount of melanin. On the other hand, a small change in the melanin concentration $\rho m$ does not cause a significant change in the absorption coefficient vector a. Therefore, the roughly estimated melanin concentration ρm0 may be employed as the melanin concentration ρm without causing a significant problem to occur.

In order to determine the estimated melanin concentration ρm0 more accurately, the estimated melanin concentration ρm0 may be determined by visually comparing the skin color and color samples. Alternatively, the estimated melanin concentration ρm0 may be determined by comparing each RGB luminance value in the captured image data 21 with RGB values of color samples.

When the concentration of melanin contained in the skin, for which the hemoglobin concentration ρh is to be estimated, is ρm0, the slope at ρm=ρm0 on each graph is {aR, aG, aB}. This can be expressed by a mathematical formula (8) shown below.

[Math 8]

$$\vec{a} = -\frac{\partial \log \vec{V}}{\partial \rho}\bigg|_{\rho=\rho_0} \quad (8)$$

$$\begin{cases} a_R = -\frac{\partial \log R}{\partial \rho}\bigg|_{\rho=\rho_0} \\ a_G = -\frac{\partial \log G}{\partial \rho}\bigg|_{\rho=\rho_0} \\ a_B = -\frac{\partial \log B}{\partial \rho}\bigg|_{\rho=\rho_0} \end{cases}$$

Here, when ρm0 is known, this known value may be used. However, in general, this value is unknown. In this case, for example, the estimated melanin concentration ρm0 may be determined from the skin color based on color samples such as color bars shown in FIG. 8A to 8C.

Next, the coefficient calculation unit 13 calculates the extraction coefficient vector x orthogonal to the absorption coefficient vector a and to the shade vector e obtained in S23 (S25). The calculated extraction coefficient vector x is stored as the extraction coefficient data 23 in the storage unit 20 in association with the imaging apparatus 2 and with the estimated melanin concentration ρm0.

The concentration calculation unit 30 acquires captured image data 21 (a camera output V) of a target for which the hemoglobin concentration ρh is to be calculated (S27). Here, let it be assumed that the melanin concentration of a target part in the acquired captured image data 21 has a value equal to the estimated melanin concentration ρm0. In this case, the concentration calculation unit 30 acquires the extraction coefficient vector x, associated with the imaging apparatus 2 that has captured the captured image data 21 and associated with the estimated melanin concentration ρm0, from the extraction coefficient data 23. The concentration calculation unit 30 estimates the hemoglobin concentration ρh by calculating −log (V)·x (S29).

As described above, with the pigment concentration calculation device according to the present embodiment, in a case where the subject 1 is, for example, a skin of a human body, it is possible to change the absorption coefficient vector a more appropriately depending on the presence or absence of sunburn, a difference in a skin color depending on a race, and/or the like. Thus, the extraction coefficient vector x can be calculated more accurately. As a result, the concentration of the desired pigment can be calculated more accurately.

(Modifications)

Pigment concentration calculation devices according to modifications of the present embodiment are described below.

(a) In one modification, in the graphs shown in FIGS. 8A to 8C, the range of the melanin concentration is divided into a plurality of categories, an absorption coefficient vector a and an extraction coefficient vector x are calculated, in advance, in each category based on representative values (slopes) of the category (concentration range). A specific example is described below in which the range of the melanin concentration is divided into three categories. Note that there is no particular restriction on the number of the divided ranges.

For example, the range of melanin concentration is divided into three categories corresponding to three categories of skin colors: a fair skin color; a standard skin color; and a dark skin color. The range of the melanin concentration ρm of each category may be determined, for example, with reference to a color sample such as a color bar. The coefficient determination unit 10 calculates the absorption coefficient vector a at the representative concentration value (for example, a median value) in each category using formula (8) described above. Then, the extraction coefficient vector x in each category is determined from the corresponding one of the calculated absorption coefficient vectors a, and stored in the storage unit 20. The concentration calculation unit 30 selects a suitable category (a category corresponding to the estimated melanin concentration ρm0) from the three categories, reads out the extraction coefficient vector x associated with the category from the storage unit 20, and uses it.

Note that a shade vector may not be used in determining the extraction coefficient vector x. This can be understood by referring to the description of the modification (g) in Embodiment 1, and thus a further description thereof is omitted.

The above explanation can be summarized as follows. That is, in the coefficient determination device (the coefficient determination unit 10) according to one aspect of the present disclosure, a plurality of categorized concentration ranges are set in advance by dividing a concentration range of a component concentration of a certain specific pigment (a non-target pigment, for example, melanin) other than the desired one pigment (for example, hemoglobin) into the plurality of categorized concentration ranges, the first response mode is represented by an absorption coefficient vector whose components are given by proportional coefficients of linear functions that approximately represent degrees of changes in additive inverses of logarithms of the respective types of luminance values that occur in response to a change in the component concentration of the specific pigment, the absorption coefficient vector is determined separately for each of the plurality of categorized concentration ranges, and the coefficient calculation unit 13 calculates the coefficients by (i) determining an extraction coefficient vector that is orthogonal to both the shade vector and the absorption coefficient vector associated with the categorized concentration range corresponding to the component concentration of the specific pigment in the specific region of the subject, and employing the respective components of the resultant extraction coefficient vector as the coefficients, or (ii) determining the absorption coefficient vector associated with the categorized concentration range corresponding to the component concentration of the specific pigment in the specific region of the subject for each of two or more types of specific pigments, and further determining an extraction coefficient vector that is orthogonal to all of the determined two or more absorption coefficient vectors, and employing the respective components of the resultant extraction coefficient vector as the coefficients.

As described above, according to the one modification, the pigment concentration calculation device is capable of calculating the extraction coefficient vector x more accurately depending on the skin type of the subject 1 based on the estimated melanin concentration ρm0, and is capable of calculating the concentration of the desired pigment accurately.

(b) In another modification, a formula for calculating the extraction coefficient vector x from the estimated melanin concentration ρm0 is given in advance by a higher-order function or another function that represents a relationship between the estimated melanin concentration and the extraction coefficient vector x.

For example, by differentiating the graphs shown in FIGS. 5A to 5C by the melanin concentration ρm, relationships between the melanin concentration ρm and the respective components (aR, aG, aB) of the absorption coefficient vector a can be obtained. Higher-order functions are then determined which fit the relationships (graphs) obtained above by the differentiation. Thus, it is possible to obtain the function for determining the absorption coefficient vector a from the melanin concentration ρm.

Next, the coefficient determination unit 10 determines the vector product of the shade vector e and the absorption coefficient vector a represented by the function of the melanin concentration ρm. As a result, the extraction coefficient vector x is calculated in advance as a function of the melanin concentration ρm. The coefficient determination unit 10 stores the relational expression (the derivation function) representing the extraction coefficient vector x in the storage unit 20. The concentration calculation unit 30 calculates the hemoglobin concentration by substituting the estimated melanin concentration ρm0 into the above-described relational expression.

The above explanation can be summarized as follows. That is, in the coefficient determination device (the coefficient determination unit 10) according to one aspect of the present disclosure, the first response mode is represented by an absorption coefficient vector obtained such that relationships are determined between a change in a component concentration of a specific pigment (a non-target pigment, such as melanin) other than the desired one pigment (for example, hemoglobin) and degrees of change in the additive inverses of the logarithms of the respective types of luminance values, and components of the absorption coefficient vector are given by approximation functions approximately representing results obtained when the relationships are differentiated with respect to the component concentration of the specific pigment, the coefficient calculation unit 13 calculates the coefficients such that (i) an extraction coefficient vector is given by a vector product of the shade vector and the absorption coefficient vector such that each component of the extraction coefficient vector is a derivation function including, as a variable of the deviation function, the component concentration of the specific pigment, and (ii) the coefficients are given by the extraction coefficient vector obtained as a result of substituting a measured value or an estimated value of the component concentration of the specific pigment in a specific region of the subject into the derivation functions.

As described above, according to the one modification, the pigment concentration calculation device is capable of calculating the extraction coefficient vector x more accurately depending on the skin type of the subject 1 based on the estimated melanin concentration ρm0, and is capable of calculating the concentration of the desired pigment accurately.

Embodiment 3

Another embodiment of the present disclosure is described below. For convenience of explanation, same reference symbols are used to denote elements having same functions as those of elements which have been described in the previous embodiment, and further duplicated explanations thereof are omitted.

Figure 9:
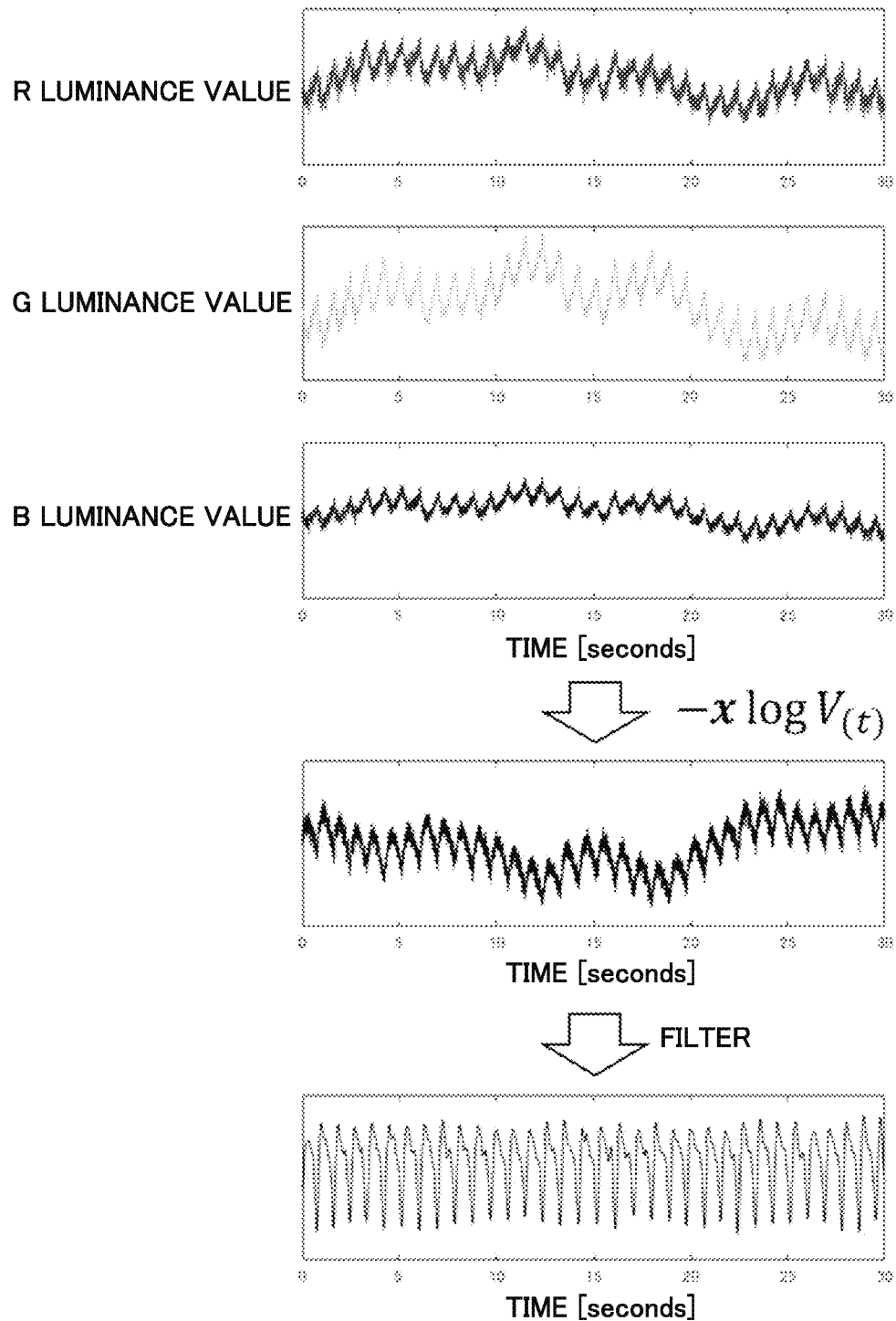
FIG. 9 is a diagram illustrating a result obtained when a pulse wave is extracted by applying an extraction coefficient vector to a time-varying output provided by an imaging apparatus.

In a pigment concentration calculation device according to the present embodiment, a moving image is input from the imaging apparatus 2, and for example, a pulse wave can be obtained using the pigment concentration calculation device. This is described below with reference to FIG. 9. FIG. 9 is a diagram showing a result of extracting a pulse wave by applying the extraction coefficient vector x to a time-varying camera output V(t).

A moving image, which is a time-varying camera output V=(VR, VG, VB) is input from the imaging apparatus 2 to the storage unit 20, and the time-varying camera output V(t) is used as the captured image data 21. In this case, the camera output V(t) obtained by imaging the same region of the skin may be stored in a matrix such that RGB luminance values are arranged in time series in a row direction while RGB luminance values associated with each same time are arranged in a column direction.

By multiplying the additive inverse of the logarithm of this matrix, −log(V(t)), by the extraction coefficient vector x from the left, a change with time in the hemoglobin concentration ρh can be obtained. The hemoglobin concentration ρh is proportional to the amount of hemoglobin per unit volume inside the skin. Therefore, the change with time in the hemoglobin concentration ρh is obtained in the form of a pulse wave.

In the pigment concentration calculation device according to the present embodiment, a filtering process may be performed on the obtained pulse wave. A lowermost diagram in FIG. 9 shows a result of performing 0.75-to-4.00-Hz bandpass filtering on the change with time in the hemoglobin concentration ρh.

As described above, by using the pigment concentration calculation device according to the present embodiment, it is possible to detect a pulse wave by a relatively simple calculation process.

Embodiment 4

Another embodiment of the present disclosure is described below. For convenience of explanation, same reference numerals are used to denote elements having same functions as those of elements described in the previous embodiment, and duplicated explanations thereof are omitted.

In the pigment concentration calculation device according to one aspect of the present disclosure, there is no particular restriction on the specific calculation method as long as the extraction coefficients can be calculated using the above-described knowledge on which the present disclosure is based. That is, it suffices if it is possible to determine a response mode (extraction coefficients) which is independent of response modes (coefficients related to pigments and coefficients related to shadow intensities) in which the imaging apparatus provides outputs in response to known components.

In one embodiment of the present disclosure, the pigment concentration calculation device calculates the extraction coefficients by a matrix operation. For example, let aR, aG, and aB denote coefficients representing a response mode in which the imaging apparatus provides outputs of R, G, and B, respectively, depending on a change in the melanin concentration. Furthermore, let eR, eG, and eB denote coefficients representing response modes in which the imaging apparatus provides outputs of R, G, and B, respectively, depending on a change in the shade intensity.

If a matrix X in the following equation (9) has an inverse matrix, then extraction coefficients are given by $x_{11}$, $x_{12}$, and $x_{13}$ in the following equation (10). Note that r1, r2, and r3 are arbitrary numbers.

[Math 9]
$$X = \begin{pmatrix} r_1 & a_R & e_R \\ r_2 & a_G & e_G \\ r_3 & a_B & e_B \end{pmatrix} \quad (9)$$

[Math 10]
$$X^{-1} = \begin{pmatrix} x_{11} & x_{12} & x_{13} \\ x_{21} & x_{22} & x_{23} \\ x_{31} & x_{32} & x_{33} \end{pmatrix} \quad (10)$$

[Examples of Implementations by Software]

Control blocks (in particular, the coefficient determination unit 10 and the concentration calculation unit 30) of the pigment concentration calculation device 100 may be realized by logic circuits (hardware) formed in an integrated circuit (an IC chip) or the like, or may be realized by software.

In the latter case, the pigment concentration calculation device 100 includes a computer that executes instructions of a program that is software that realizes each function. The computer includes at least one processor (a control apparatus) or the like and at least one computer-readable storage medium in which the program is stored. In the computer, the processor reads the program from the storage medium and executes the program, thereby achieving an object of the present disclosure. For example, a CPU (Central Processing Unit) may be used as the processor. The storage medium may be a "non-transitory tangible medium", such as a read-only memory (ROM), a tape, a disk, a card, a semiconductor memory, a programmable logic circuit, or the like. A RAM (Random Access Memory) or the like for loading the program may also be provided. Alternatively, the program may be supplied to the computer via a transmission medium (a communication network, a broadcast wave, or the like) capable of transmitting the program. Note that an aspect of the present disclosure may also be realized in the form of a data signal embedded in a carrier wave such that the program is embodied by electronic transmission.

Note that the present disclosure is not limited to the embodiments described above, and various modifications are possible within the scope described in claims. Embodiments obtained by combining the technical means disclosed in the embodiments also fall within the technical scope of the present disclosure. A new technical feature may be achieved by combining technical means disclosed in the embodiments.

The invention claimed is:

1. A coefficient determination device configured to determine, based on captured image data obtained by imaging a subject including one or more types of pigments, a plurality of coefficients included in a function used to calculate a concentration of a desired pigment in a specific region of the subject, the captured image data being data obtained by using a predetermined imaging apparatus and having a plurality of types of luminance values representing luminances in respective wavelength bands, the function including the plurality of types of luminance values as a plurality of variables, each coefficient in the plurality of coefficients corresponding to a respective variable in the plurality of variables, and the plurality of coefficients being obtained in association with the predetermined imaging apparatus, the coefficient determination device comprising:

a response calculation unit configured to calculate at least one of following response modes:

a first response mode indicating a relationship between a change in a component concentration of a pigment other than the desired pigment and a change in each of the plurality of types of luminance values in the captured image data, and a second response mode indicating a relationship between a change in a shade intensity and a change in each of the plurality of types of luminance values in the captured image data; and a coefficient calculation unit configured to calculate the plurality of coefficients using at least one of the first and second response modes, wherein the second response mode is represented as a shade vector including parameters as components respectively indicating degrees of changes in additive inverses of logarithms of the plurality of types of luminance values caused by the change in the shade intensity.

2. The coefficient determination device according to claim 1, wherein the response calculation unit calculates the second response mode based on a spectral sensitivity of the predetermined imaging apparatus.

3. The coefficient determination device according to claim 2, wherein the response calculation unit calculates the first response mode based on a light absorption spectrum of a pigment other than the desired pigment and on the spectral sensitivity of the predetermined imaging apparatus.

4. The coefficient determination device according to claim 1, wherein the response calculation unit calculates the first response mode based on a light absorption spectrum of a pigment other than the desired pigment and on a spectral sensitivity of the predetermined imaging apparatus.

5. The coefficient determination device according to claim 1, wherein the first response mode is represented such that in a case that, for a certain pigment other than the desired pigment, the degree of change in the additive inverse of the logarithm of each of the plurality of types of luminance values caused by the change in the component concentration of the certain pigment is approximately expressed by a linear function, the first response mode is represented by an absorption coefficient vector components of which are given by proportional coefficients in the respective linear functions.

6. The coefficient determination device according to claim 5, wherein the coefficient calculation unit calculates the plurality of coefficients such that the coefficients are given by respective components of an extraction coefficient vector orthogonal at least to one of the shade vector and the absorption coefficient vector associated with a pigment other than the desired pigment.

7. The coefficient determination device according to claim 1, wherein
a plurality of categorized concentration ranges is set in advance by dividing a concentration range of a component concentration of a specific pigment other than the desired pigment into the plurality of categorized concentration ranges,
the first response mode is represented by an absorption coefficient vector, components of which are given by proportional coefficients of linear functions that approximately represent degrees of changes in additive inverses of logarithms of the respective types of luminance values that occur in response to a change in the component concentration of the specific pigment,
the absorption coefficient vector is determined separately for each of the plurality of categorized concentration ranges, and
the coefficient calculation unit calculates the coefficients by:
determining an extraction coefficient vector that is orthogonal to both the shade vector and the absorption coefficient vector associated with each of the plurality of categorized concentration ranges corresponding to the component concentration of the specific pigment in the specific region of the subject, and employing respective components of the extraction coefficient vector as the coefficients,
or
determining the absorption coefficient vector associated with each of the plurality of categorized concentration ranges corresponding to the component concentration of the specific pigment in the specific region of the subject for each of two or more types of specific pigments, and further determining an extraction coefficient vector that is orthogonal to all of the determined two or more absorption coefficient vectors, and employing respective components of the extraction coefficient vector as the coefficients.

8. The coefficient determination device according to claim 1, wherein
the first response mode is represented by an absorption coefficient vector obtained such that relationships are determined between a change in a component concentration of a specific pigment other than the desired pigment and degrees of change in the additive inverses of the logarithms of the respective types of luminance values, and components of the absorption coefficient vector are given by approximation functions approximately representing results obtained when the relationships are differentiated with respect to the component concentration of the specific pigment, and
the coefficient calculation unit calculates the coefficients such that:
an extraction coefficient vector is given by a vector product of the shade vector and the absorption coefficient vector such that each component of the extraction coefficient vector is a derivation function including, as a variable of the deviation function, the component concentration of the specific pigment, and
the coefficients are given by the extraction coefficient vector obtained as a result of substituting a measured value or an estimated value of the component concentration of the specific pigment in the specific region of the subject into the derivation functions.

9. A pigment concentration calculation device comprising:
the coefficient determination device according to claim 1, wherein
a concentration calculation unit is configured to calculate the concentration of the desired pigment in the specific region of the subject in the captured image data by using the coefficients determined by the coefficient determination device, such that the concentration of the desired pigment is calculated based on products obtained when the additive inverses of the logarithms of the plurality of types of luminance values are multiplied by the coefficients.

10. The pigment concentration calculation device according to claim 9, further comprising the predetermined imaging apparatus,
wherein the predetermined imaging apparatus is a Red, Green, and Blue (RGB) camera.

11. The pigment concentration calculation device according to claim 10, wherein
the one or more types of pigments include a melanin pigment and a hemoglobin pigment, and
the desired pigment is the hemoglobin pigment.

12. The pigment concentration calculation device according to claim 9, wherein
the one or more types of pigments include a melanin pigment and a hemoglobin pigment, and
the desired pigment is the hemoglobin pigment.

13. A coefficient determination device configured to determine, based on captured image data obtained by imaging a subject including one or more types of pigments, a plurality of coefficients included in a function used to calculate a concentration of a desired pigment in a specific region of the subject,
the captured image data being data obtained by using a predetermined imaging apparatus and having a plurality of types of luminance values representing luminances in respective wavelength bands, the function including the plurality of types of luminance values as a plurality of variables, each coefficient in the plurality of coefficients corresponding to a respective variable in the plurality of variables, and the plurality of coefficients being obtained in association with the predetermined imaging apparatus, the coefficient determination device comprising:
a response calculation unit configured to calculate at least one of following response modes:
a first response mode indicating a relationship between a change in a component concentration of a pigment other than the desired pigment and a change in each of the plurality of types of luminance values in the captured image data, and
a second response mode indicating a relationship between a change in a shade intensity and a change in each of the plurality of types of luminance values in the captured image data; and
a coefficient calculation unit configured to calculate the plurality of coefficients using at least one of the first and second response modes,
wherein, in the coefficient calculation unit, a sum of numbers of the first and second response modes is smaller than a number of the plurality of types of luminance values.

14. A coefficient determination method for determining, based on captured image data obtained by imaging a subject including one or more types of pigments, a plurality of coefficients included in a function used to calculate a concentration of a desired pigment in a specific region of the subject, the captured image data being data obtained by using a predetermined imaging apparatus and having a plurality of types of luminance values representing luminances in respective wavelength bands, the function including a plurality of types of luminance values as a plurality of variables, each coefficient in the plurality of coefficients corresponding to a respective variable in the plurality of variables, and the plurality of coefficients being obtained in association with the predetermined imaging apparatus, the coefficient determination method comprising:

calculating at least one of following response modes:
- a first response mode indicating a relationship between a change in a component concentration of a pigment other than the desired pigment and a change in each of the plurality of types of luminance values in the captured image data, and
- a second response mode indicating a relationship between a change in a shade intensity and a change in each of the plurality of types of luminance values in the captured image data; and calculating the plurality of coefficients using at least one of the first and second response modes, wherein the second response mode is represented as a shade vector including parameters as components respectively indicating degrees of changes in additive inverses of logarithms of the plurality of types of luminance values caused by the change in the shade intensity.

15. A non-transitory computer-readable storage medium storing a program that causes a computer to function as the coefficient determination device according to claim 1.

* * * * *